United States Patent [19]

Tyrer et al.

[11] 4,172,227
[45] Oct. 23, 1979

[54] FLOW MICROFLUOROMETER

[75] Inventors: Harry W. Tyrer, Durham; Capers W. McDonald, Raleigh, both of N.C.

[73] Assignee: Becton, Dickinson and Company, Rutherford, N.J.

[21] Appl. No.: 926,759

[22] Filed: Jul. 21, 1978

[51] Int. Cl.² ............... G01N 21/38; G01N 21/56
[52] U.S. Cl. .................. 250/461 B; 356/417
[58] Field of Search ............. 250/458, 461 B, 461 R; 356/317, 318, 417

[56] References Cited

U.S. PATENT DOCUMENTS

| | | | |
|---|---|---|---|
| 3,470,373 | 9/1969 | Brewer et al. | 250/461 R |
| 3,497,690 | 2/1970 | Wheeless, Jr. et al. | 250/461 R |
| 3,586,859 | 6/1971 | Katz et al. | 250/459 |
| 3,864,571 | 2/1975 | Stillman et al. | 250/302 |
| 3,885,879 | 5/1975 | Louder et al. | 356/189 |
| 3,916,197 | 10/1975 | Fulwyler | 250/361 |
| 3,918,812 | 11/1975 | Holm | 250/461 B |
| 3,973,129 | 8/1976 | Blumberg et al. | 250/461 B |

Primary Examiner—Alfred E. Smith
Assistant Examiner—Janice A. Howell
Attorney, Agent, or Firm—Gerald J. Ferguson, Jr.; Joseph J. Baker

[57] ABSTRACT

In an improved flow microfluorometer, the variation in fluorescence intensity of a particle as a function of wavelength is transduced to an electrical variation in time where time in the signal variation is proportional to wavelength. The resulting spectrum may be a line spectrum or a continuous spectrum. The temporal waveforms can then be analyzed to extract data on a single particle, and this information in turn can be used as a means to identify the particle for sorting.

20 Claims, 3 Drawing Figures

FLOW MICROFLUOROMETER

BACKGROUND OF THE INVENTION

This invention relates to flow microfluorometers and in particular to an improved flow microfluorometer wherein the entire fluorescence emission spectrum of particles can be rapidly obtained.

As is known, the fluoroscence spectrum of stained or unstained particles such as human cells can yield valuable information as to the nature of the cell and/or the condition of the cells. For example, the emission spectra of various stained particles within the blood are different. Thus, a count of the different types of white blood cells can be obtained since the emission spectra of these cells are different. Further, it is known the emission spectra of certain stained cancer cells are different from those of normal cells in certain tissues of the body. Again, the differences in emission spectra can be utilized to detect the abnormal presence of pathogenic cells.

It is known to accumulate spectra on individual cells by static single cell analysis or upon a stationary solution containing a number of cells, such as disclosed in U.S. Pat. Nos. 3,470,373; 3,497,690; 3,918,812; and 3,973,129. Further, it is known on a static basis to project a real image of a cell to a predetermined point, there being disposed at a point of rotating or oscillating wedge filter or grating whereby a continuous fluorescence emission spectrum of the static cell can be obtained. However, the accumulation of spectrum information is quite slow due to the static nature of the procedure. The use of a wedge filter in a spectrophotometer is also disclosed in U.S. Pat. No. 3,885,879.

Data can be more rapidly accumulated by dynamic single cell analysis in flow microfluorometers where cells are permitted to pass through an excitation light beam to effect fluoroscence thereof where, for example, 500–5,000 cells per second can flow through the beam. Such flow microfluorometers are disclosed, for example, in U.S. Pat. Nos. 3,586,859; 3,864,571; and 3,916,197. In some of the latter microfluorometers, at least two filters are employed, each of which passes a different wavelength of the fluorescence emissions spectrum of the activated particles. The filter outputs are then respectively focused at at least two different photomultiplier tubes. The outputs of the photomultiplier tubes are then combined for appropriate signal processing.

The resolution of the foregoing flow delivery systems is low in that only two wavelength portions or lines are detected out of the entire fluorescence emission spectrum of the particles. It is possible to increase this resolution by employing more filters and accordingly more photomultiplier tubes, there being, as indicated above, one photomultiplier tube for each filter. Of course, the resolution can be increased in this manner only to a certain point at which either space limitations or cost limitations occur. Not only is each photomultiplier tube expensive but also there are many applications where space is at a premium.

A further limitation of the above described microfluorometers is that the light supplied to the filters is divided between the filters. Hence, the light available at each filter output for detection is somewhat reduced thus rendering the system somewhat inefficient.

SUMMARY OF THE INVENTION

It is accordingly a primary object of this invention to provide an improved flow microfluorometer system and method whereby a continuous or line fluorescence emission spectrum of a particle can be rapidly obtained.

It is a further object of this invention to provide an improved microfluorometer and method of the above type wherein a single light detector is employed.

It is a further object of this invention to provide an improved microfluorometer and method of the above type where the fluorescence emission spectrum of the particle is rapidly obtained in a sequential manner.

It is a further object of this invention to provide an improved microfluorometer and method of the above type wherein human cells or other particles are processed.

It is a further object of this invention to provide an improved microfluorometer and method of the above type where the light is efficiently utilized at the light detector.

Other objects and advantages of this invention will be apparent from a reading of the following specification and claims taken with the drawing.

DETAILED DESCRIPTION OF A PREFERRED EMBODIMENT OF THE INVENTION

Figure 1:
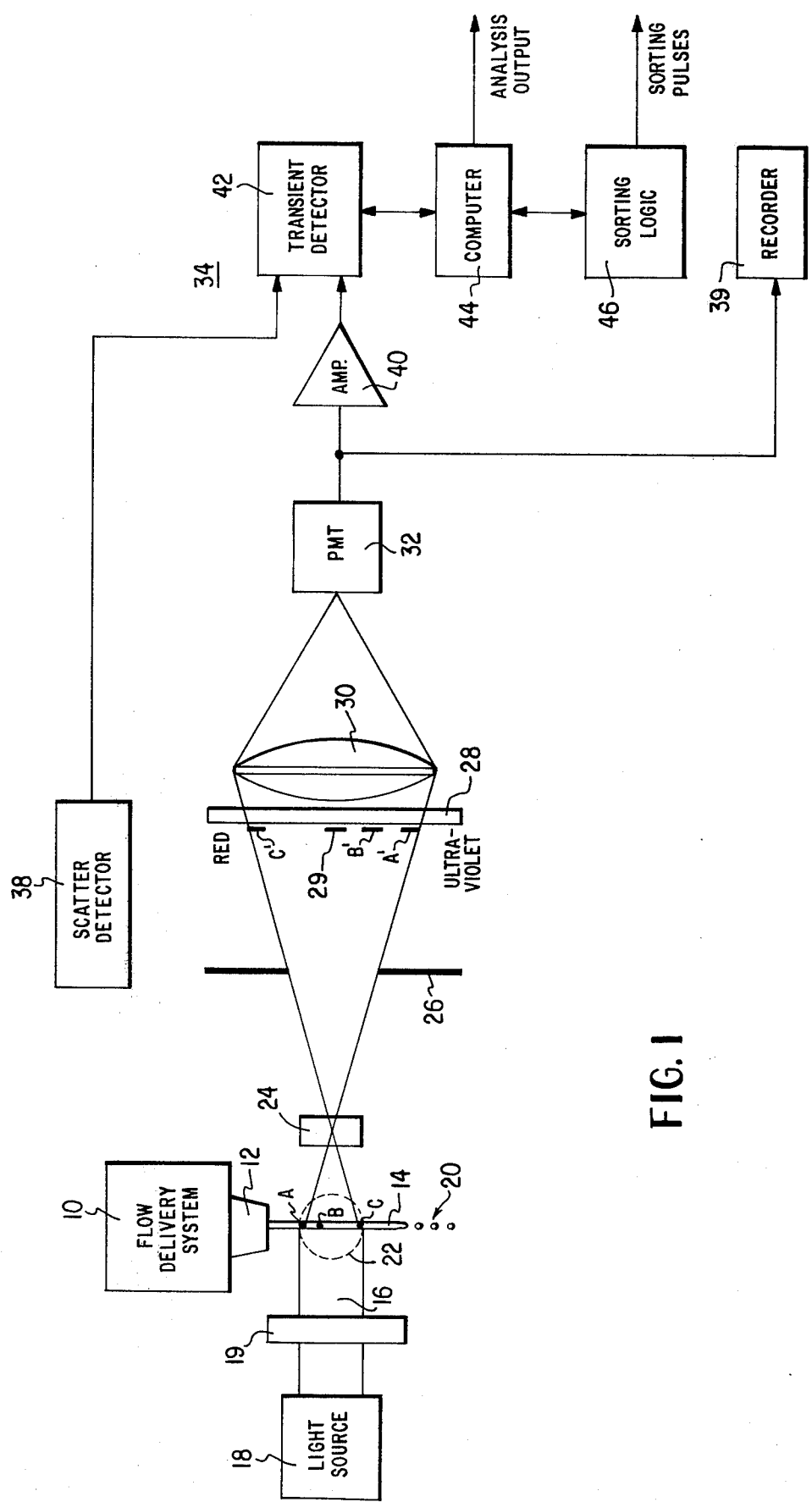
FIG. 1 is a schematic diagram of an illustrative flow microfluorometer in accordance with the invention.

Referring to FIG. 1, there is shown a flow delivery system 10 having a nozzle 12 which delivers a particle containing stream 14. The particles may either be endogenous whereby they fluoresce upon proper excitation thereof or they may be tagged with appropriate substances to effect fluorescence thereof. Further, the particles may comprise cellular matter of either the animal or plant kingdoms. Although there is no intent to be limited to a particular flow rate, typically 500–5,000 cells per second are sequentially delivered from nozzle 12 with a cell separation of 0.2-2 cm., the particles transversing a beam 16 emitted from a light source 18 where the cells pass through the beam single file. As indicated at 20, the particle containing fluid tends to break up into drops after passage through the beam. Flow delivery system 10 may correspond exactly to that incorporated in the Fluorescence Activated Cell Sorter (FACS II) manufactured by Becton, Dickinson and Company, Rutherford, N.J.

The cross-sectional area of the beam is indicated at 22 in dotted lines, the diameter thereof being typically approximately 1 millimeter. The source 18 may correspond to the laser source used in the above-mentioned Becton, Dickinson FACS II system. If so, the light source is orthogonal to the said detection system at the stream. It should be noted that a 50 micron diameter laser beam is employed in the FACS II system whereas, as mentioned above, the beam width employed in the present invention may typically be 1 millimeter. This larger diameter beam can be obtained by simply defocusing the smaller FACS II beam. Of course, laser sources are also known which are capable of generating a 1 millimeter beam. In any event, there is no intention to be limited to a particular width beam nor is there any intent to be limited to a particular type beam or source in that, for example, an ultraviolet source may also be used as source 18.

Further, a cylindrical lens or other appropriate one-dimensional converging means may be disposed as shown at 19 to converge the beam from source 18 into a line coaxial with the path through which the cells travel, the line extending between A and C in FIG. 1. By so converging the beam, the intensity thereof is limited to the path travelled by the cells to thereby optimize the utilization thereof.

A particular cell is shown in three different positions A, B and C as it passes through the beam. The cell is, of course, fluorescence activated as it passes through the beam. A lens system 24 and an iris 26 project the image of each cell onto a wedge filter 28, the image of the cell at position A being projected to position A' on filter 28, the image at position B being projected to B' and C to C'. An obscuration bar 29 acts to block the excitation at its transmission region on the wedge filter. In addition to or instead of, a barrier filter can be used to block the excitation. As indicated in FIG. 1, the lower end of filter 28 passes radiations at the ultraviolet end of the spectrum, the upper end passes red wavelengths while position B' may correspond to blue wavelengths. Hence, although the entire fluorescence emission spectrum is projected onto A' when the cell is at A, only a short wavelength portion of the spectrum (ultraviolet, for example) is passed by the filter. At B', a longer wavelength portion is passed (blue, for example) while at C' the longest wavelength portion of the spectrum is passed (red, for example).

The radiations transmitted from filter 28 are sequentially focused by a collecting lens 30 onto a photomultiplier tube 32. That is, when the cell image is at A', the shorter wavelength portion of the fluorescence emission spectrum is focused onto the photomultiplier tube. As the cell passes through the beam 16, successively longer wavelength portions of the emission spectrum will be focused at tube 32 until the cell image reaches C' at which time the longest wavelength of interest will be directed to the tube. Hence, the output signal from photomultiplier tube 32 which is applied to a signal processor 34 and a recorder 39 is at time varying signal, the time axis thereof being proportional to wavelength and the voltage or current output being proportional to the emission intensity at a particular wavelength. It can thus be seen from the foregoing that this invention provides a unique method for scanning the entire fluorescence emission spectrum of particles such as cells, this being effected by projecting the moving image of the particle as it passes through an excitation beam onto a wedge filter which thereby sequentially transmits increasingly longer (shorter) wavelength portions of the spectrum to a detection device including lens 30 and tube 32. In lieu of wedge filter 28, other optical dispersion means may be used such as a prism or grating where suitable geometry would be employed and the principle would be the same. Also, in lieu of lens 30 and tube 32, a linear light sensitive, diode array may be placed in the position of lens 30 adjacent filter 28 whereby the lowest diode would be responsive to the ultraviolet portion (for example) of the spectrum and the highest, the red portion (for example) thereof. In this case, the outputs from the diodes would still occur sequentially; however, they would be in parallel and suitable for processing by appropriate circuitry. It should also be noted that although the wedge filter 28 has been shown with the red end thereof at the top and the ultraviolet end at the bottom, these ends could be reversed so that red occurs at the bottom and ultraviolet at the top. The spectrum as generated above is the so-called uncorrected spectrum and may be corrected by correcting for the system transmission function either electronically or by the use of spatial filters as is known in this art.

Figure 2:
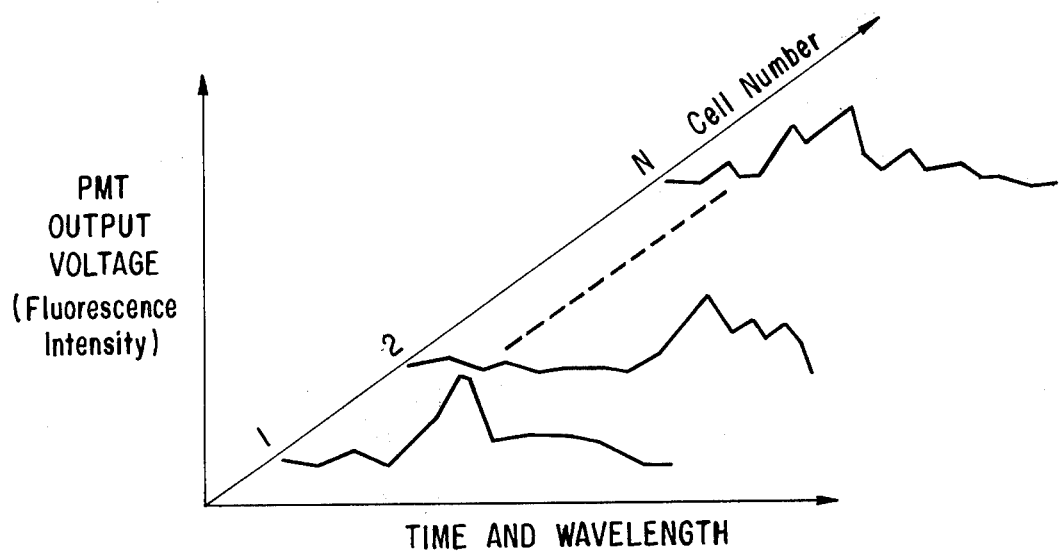
FIG. 2 is an illustrative X-Y oscilloscope display of the spectrum of N cells in accordance with the invention.

The output signal from photomultiplier tube 32 is applied to a signal processor generally indicated at 34 the operation of which may be initiated by the output of a scatter detector 38. Scatter detector 38 is responsive to light scattered from each cell when it reaches point A. That is, prior to the cell reaching point A, it does not fluoresce. Upon reaching point A, the fluorescence is activated by the laser beam and, in addition to the rays projected through lens system 24 and iris 26, there are rays which impinge upon detector 38. Detector 38 includes a photodetecting element and may correspond exactly to the scatter detector used in the above-mentioned FACS II system. Photomultiplier tube 32 may also correspond to the tube used in the FACS II system as may lens system 24 and iris 26. Scatter detector 38 thus signals to processor 34 the presence of a particle in beam 16. The output from photomultiplier tube 32 may also be applied to a recorder 39 such as an oscilloscope where the fluorescence spectrum may be visually inspected and photographed if desired. For example, an X-Y oscilloscope may be employed to isometrically display each pulse (or cell) as shown in FIG. 2.

Figure 3:
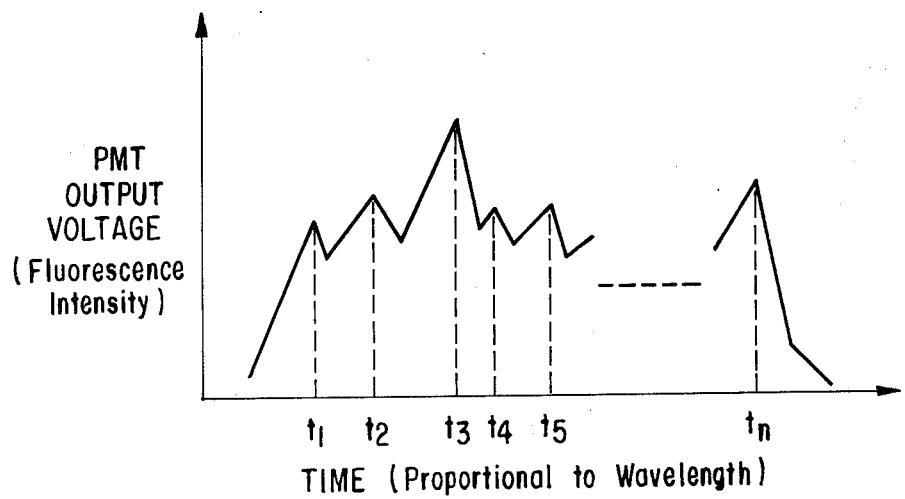
FIG. 3 is a graph which illustrates the temporal variation of the spectrum of a cell and how different wavelengths can be obtained at different points in time.

Signal processor 34 effects the extraction of more information. Thus, it permits analysis of the entire output waveform from tube 32 and computer analysis of the entire cell population. Thus, the output waveform is applied to a transient waveform detector 42 via an amplifier 40 and then fed to a computer 44. Detector 42 and computer 44 are commercially available and the sorting logic may be the same as that used in the FACS II system. With appropriate a priori knowledge, it is possible to quantitate those compounds which fluoresce in the particle. Wavelength variation in spectra can be obtained at different points in time as indicated in FIG. 3. Each $t_i$ corresponds to a particular fluorescence wavelength, and the value of n is determined by the overall resolution of the chemical (tagging) optical and electronics system. An appropriate data reduction schema may be used to obtain descriptors of the spectrum which then may be used as a means of identifying similar cell types.

It is possible to physically isolate cell types according to the values of fluorescence at a particular wavelength or by use of the descriptors. Since the grouping of the cells is dependent upon its identification, it suffices only to find the appropriate means of analysis and to sort in accordance with sorting logic 46 on the basis of this analysis, as is possible on the cell sorter-type of instrument. Care is required to consider uniqueness for the descriptors and the time available to perform the sorting operation.

It is apparent that many schemes exist to analyze and sort cells on the basis of their fluorescence spectra as measured in the present invention. For example, one can measure the fluorescence depolarization spectrum of single particles by appropriately splitting the emission beam with polarizing filters and using two of the units of the present invention.

Both the parallel and perpendicular fluorescence quantities are available for calculation using the approach of processor 34 of FIG. 1. Many other examples can be implemented by using alternate schemes with the unit of the present invention and appropriate electronics.

What is claimed is:

1. Apparatus for producing the fluorescence emission spectrum of particles comprising
    means for passing said particles through an excitation light beam to effect fluorescence thereof; and
    detecting means for detecting predetermined wavelengths of the said fluorescence emission spectrum of each particle, each detected wavelength being a function of the position of said particle with respect to said detecting means as it passes through the excitation light beam.

2. Apparatus as in claim 1 where said detecting means includes
    optical dispersion means having at least a first surface;
    means for projecting an image of each of said particle onto said optical dispersion means so that the particle image moves across said first surface as the particle passes through said excitation beam, said optical dispersion means including means for passing predetermined wavelengths of said fluorescence emission spectrum of the particle depending on the position of said particle image with respect to said first surface of said optical dispersion means; and
    converting means for converting the output from said optical dispersion means to at least one electrical signal representative of at least one of the said predetermined wavelengths of the fluorescence emission spectrum.

3. Apparatus as in claim 2 where said converting means comprises a single light sensitive means for converting incident light thereon to electricity and where said detecting means includes focusing means for focusing the output from said optical dispersion means onto said single light sensitive means to produce said one electrical signal which varies with time so that said predetermined wavelengths of the fluorescence emission spectrum correspond to respective predetermined points in time of the electrical signal.

4. Apparatus as in claim 2 where said optical dispersion means comprises a wedge filter.

5. Apparatus as in claim 2 where said optical dispersion means comprises a prism.

6. Apparatus as in claim 2 where said optical dispersion means comprises a grating.

7. Apparatus as in claim 1 where said predetermined wavelengths of said fluorescence emission spectrum constitutes a continous spectrum.

8. Apparatus as in claim 1 where said particles are cells selected from the animal kingdom.

9. Apparatus as in claim 1 including means for generating said excitation light beam with a laser.

10. Apparatus as in claim 1 where said detecting means sequentially detects said predetermined wavelengths to provide a time varying signal representative of said fluorescence emission spectrum.

11. Apparatus as in claim 10 including means for processing said time varying signal to select therefrom portions corresponding to certain ones of said predetermined wavelengths.

12. Apparatus as in claim 1 including means for converging said excitation light beam into a line coaxial with the path through which said particles pass.

13. Apparatus as in claim 1 where said means for passing the particles includes means for flowing said particles single file through said excitation light beam.

14. Apparatus for scanning the fluorescence emission spectrum of particles comprising
    a light beam source for producing an excitation light beam;
    means for passing said particles through said excitation light beam to effect fluorescence thereof;
    a wedge filter;
    means for projecting an image of each said particle onto said wedge filter so that the particle image moves across the filter as the particle passes through said excitation beam, said wedge filter passing predetermined wavelengths of the said fluorescence emission spectrum of the particle depending on the position of said particle image with respect to said wedge filter; and
    means for directing said predetermined wavelengths passing through the wedge filter onto a detector to provide a time varying signal representative of said fluorescence emissison spectrum of said particles.

15. A method for producing the fluorescence emission spectrum of particles comprising the steps of
    passing said particles through an excitation light beam to effect fluorescence thereof; and
    detecting with a detecting means predetermined wavelengths of the said fluorescence emission spectrum of each particle, each detected wavelength being a function of the position of said particle with respect to said detecting means as it passes through said excitation light beam.

16. A method as in claim 15 where said particles are cells.

17. A method as in claim 15 including the step of generating said excitation light beam with a laser.

18. A method as in claim 15 where said predetermined wavelengths are sequentially detected to provide a time varying signal representative of said fluorescence emission spectrum.

19. A method as in claim 18 including the step of processing said time varying signal to select therefrom portions corresponding to certain ones of said predetermined wavelengths.

20. A method of scanning the fluorescence emission spectrum of particles comprising the steps of
    passing said particles through an excitation light beam to effect fluorescence;
    projecting an image of each said particle onto a wedge filter so that the particle image moves across the filter as the particle passes through said excitation beam, said wedge filter passing predetermined wavelengths of the said fluorescence emission spectrum of the particle depending on the position of said particle image with respect to said wedge filter; and
    directing said predetermined wavelengths passing through the wedge filter onto a detector to provide a time varying signal representative of said fluorescence emission spectrum of said particles.

* * * * *